(12) United States Patent
Sutton et al.

(10) Patent No.: US 11,607,525 B1
(45) Date of Patent: Mar. 21, 2023

(54) METHODS AND DEVICES FOR VASCULAR ACCESS

(71) Applicant: I-V Access Technology, Inc., San Francisco, CA (US)

(72) Inventors: Thomas Sutton, Summit, NJ (US); Joe Ranalleta, Greenville, SC (US); Nicholas Hogan Mininni, Wilmington, NC (US); Kevin Johnson, Hillsborough, NC (US)

(73) Assignee: I-V Access Technology, Inc., San Francisco, CA (US)

( * ) Notice: Subject to any disclaimer, the term of this patent is extended or adjusted under 35 U.S.C. 154(b) by 0 days.

(21) Appl. No.: 17/812,397

(22) Filed: Jul. 13, 2022

Related U.S. Application Data (60) Provisional application No. 63/367,403, filed on Jun. 30, 2022.

(51) Int. Cl.
*A61M 25/00* (2006.01)

(52) U.S. Cl.
CPC .... *A61M 25/0097* (2013.01); *A61M 25/0075* (2013.01); *A61M 2025/0076* (2013.01)

(58) Field of Classification Search
CPC .................. A61M 25/0075; A61M 2025/0076
See application file for complete search history.

(56) References Cited

U.S. PATENT DOCUMENTS

| | | |
|---|---|---|
| 3,195,786 A | 7/1965 | Vogt |
| 3,347,232 A | 10/1967 | Abraham |
| 3,356,093 A * | 12/1967 | Monahon .......... A61M 25/10185 604/920 |
| 3,861,416 A | 1/1975 | Wichterle |
| 4,045,009 A | 8/1977 | Pees |
| 4,341,239 A | 7/1982 | Atkinson |
| 4,387,879 A | 6/1983 | Tauschinski |
| 4,465,102 A | 8/1984 | Rupp |
| 4,524,805 A | 6/1985 | Hoffman |
| 4,565,545 A | 1/1986 | Suzuki |
| 4,588,398 A | 5/1986 | Daugherty et al. |

(Continued)

FOREIGN PATENT DOCUMENTS

| | | | |
|---|---|---|---|
| CN | 203694357 | 7/2014 | |
| EP | 316096 A * | 5/1989 | ........ A61M 39/0606 |

(Continued)

*Primary Examiner* — Nathan R Price
*Assistant Examiner* — Mark A Igel
(74) *Attorney, Agent, or Firm* — Levine Bagade Han LLP (57) ABSTRACT

A catheter assembly configured for use with a male luer is provided herein. The catheter assembly can comprise a catheter hub having an interior chamber and a valve located in the interior chamber. The valve can comprise a distal portion, a proximal portion, and a sidewall extending therebetween to define a valve interior. The valve can include a barrier layer having a concave shape that extends in the valve interior from the sidewall at the distal portion. The barrier layer can have at least one slit extending therethrough that is in a normally closed configuration to prevent a fluid from passing through the barrier layer. The catheter assembly can further comprise a sealing ring located circumferentially at a distal end of the valve distally to the barrier layer. The sealing ring can form a seal between the valve and the interior chamber at the distal end.

15 Claims, 6 Drawing Sheets

(56) References Cited

U.S. PATENT DOCUMENTS

| | | | |
|---|---|---|---|
| 4,629,450 A | 12/1986 | Suzuki et al. | |
| 4,655,752 A * | 4/1987 | Honkanen | A61M 39/06 604/167.04 |
| 4,683,916 A * | 8/1987 | Raines | F16K 15/148 137/854 |
| 4,758,225 A * | 7/1988 | Cox | A61M 5/158 604/167.03 |
| 4,924,923 A * | 5/1990 | Boehmer | B60K 15/04 277/560 |
| 4,950,257 A * | 8/1990 | Hibbs | A61M 39/0606 604/167.04 |
| 5,010,925 A * | 4/1991 | Atkinson | F16K 15/147 137/846 |
| 5,092,857 A * | 3/1992 | Fleischhacker | A61M 39/0606 604/167.04 |
| 5,114,407 A | 5/1992 | Burbank | |
| 5,114,408 A * | 5/1992 | Fleischhaker | A61M 39/0606 604/905 |
| 5,122,118 A | 6/1992 | Haber et al. | |
| 5,129,884 A | 7/1992 | Dysarz | |
| 5,176,650 A | 1/1993 | Haining | |
| 5,215,538 A * | 6/1993 | Larkin | A61M 39/26 137/859 |
| 5,242,410 A | 9/1993 | Melker | |
| 5,269,771 A * | 12/1993 | Thomas | A61M 39/26 604/167.04 |
| 5,295,658 A * | 3/1994 | Atkinson | A61M 39/045 604/905 |
| 5,405,323 A * | 4/1995 | Rogers | A61M 39/26 604/167.04 |
| 5,445,617 A | 8/1995 | Yoon | |
| 5,456,284 A * | 10/1995 | Ryan | F16K 15/147 604/167.04 |
| 5,462,255 A * | 10/1995 | Rosen | A61M 39/26 251/149.6 |
| 5,484,418 A | 1/1996 | Quiachon et al. | |
| 5,527,290 A | 6/1996 | Zadini et al. | |
| 5,533,708 A * | 7/1996 | Atkinson | F16L 29/005 604/905 |
| 5,618,272 A | 4/1997 | Nomura | |
| 5,713,876 A | 2/1998 | Bogert et al. | |
| 5,727,594 A * | 3/1998 | Choksi | F16K 15/023 137/859 |
| 5,843,046 A | 12/1998 | Motisi et al. | |
| 5,871,110 A | 2/1999 | Grimard et al. | |
| 5,957,898 A | 9/1999 | Jepson et al. | |
| 5,967,490 A | 10/1999 | Pike | |
| 6,024,729 A | 2/2000 | Dehdashtian et al. | |
| 6,035,896 A | 3/2000 | Liardet | |
| 6,142,981 A * | 11/2000 | Heck | A61M 39/0606 604/256 |
| 6,165,168 A | 12/2000 | Russo | |
| 6,168,037 B1 | 1/2001 | Grimard | |
| 6,186,997 B1 | 2/2001 | Gabbard et al. | |
| 6,261,282 B1 | 7/2001 | Jepson et al. | |
| 6,267,748 B1 | 7/2001 | Gulliksen et al. | |
| 6,352,520 B1 | 3/2002 | Miyazaki | |
| 6,390,130 B1 | 5/2002 | Guala | |
| 6,607,511 B2 | 8/2003 | Halseth et al. | |
| 6,702,255 B2 | 3/2004 | Dehdashtian | |
| 6,706,017 B1 | 3/2004 | Dulguerov | |
| 6,716,197 B2 | 4/2004 | Svendsen | |
| 6,817,989 B2 | 11/2004 | Svendsen et al. | |
| 7,001,396 B2 | 2/2006 | Glazier et al. | |
| 7,470,254 B2 | 12/2008 | Basta et al. | |
| 7,658,725 B2 | 2/2010 | Bialecki et al. | |
| 7,736,339 B2 | 6/2010 | Woehr et al. | |
| 7,736,342 B2 | 6/2010 | Abriles et al. | |
| 7,744,571 B2 | 6/2010 | Fisher et al. | |
| 7,753,338 B2 | 7/2010 | Desecki | |
| 7,892,209 B2 | 2/2011 | Harand et al. | |
| 7,914,519 B2 | 3/2011 | Moran et al. | |
| 7,938,805 B2 | 5/2011 | Harding et al. | |
| 7,947,032 B2 | 5/2011 | Harding et al. | |
| 8,006,953 B2 | 8/2011 | Bennett | |
| 8,021,338 B2 | 9/2011 | Adams | |
| 8,092,432 B2 | 1/2012 | Nordgren | |
| 8,105,288 B2 | 1/2012 | Keyser et al. | |
| 8,251,923 B2 | 8/2012 | Carrez et al. | |
| 8,361,020 B2 | 1/2013 | Stout | |
| 8,469,928 B2 | 6/2013 | Stout et al. | |
| 8,579,870 B2 | 11/2013 | Willis et al. | |
| 8,591,469 B2 | 11/2013 | Keyser et al. | |
| 8,647,312 B2 | 2/2014 | Utterberg et al. | |
| 8,758,306 B2 | 6/2014 | Lopez et al. | |
| 8,900,192 B2 | 12/2014 | Anderson et al. | |
| 8,915,884 B2 | 12/2014 | Tal et al. | |
| 8,932,259 B2 | 1/2015 | Stout et al. | |
| 9,028,425 B2 | 5/2015 | Burkholz | |
| 9,095,683 B2 | 8/2015 | Hall et al. | |
| 9,114,231 B2 | 8/2015 | Woehr et al. | |
| 9,149,625 B2 | 10/2015 | Woehr et al. | |
| 9,155,863 B2 | 10/2015 | Isaacson et al. | |
| 9,155,864 B2 | 10/2015 | Stout et al. | |
| 9,427,549 B2 | 8/2016 | Woehr et al. | |
| 9,604,035 B2 | 3/2017 | Keyser et al. | |
| 9,764,117 B2 | 9/2017 | Bierman et al. | |
| 9,775,973 B2 | 10/2017 | Keyser et al. | |
| 9,851,268 B2 | 12/2017 | Eichhorn et al. | |
| 9,861,792 B2 | 1/2018 | Hall et al. | |
| 10,004,533 B2 | 6/2018 | Entabi | |
| 10,010,343 B2 | 7/2018 | Bierman et al. | |
| 10,052,474 B2 | 8/2018 | Keyser et al. | |
| 10,136,916 B2 | 11/2018 | Bierman et al. | |
| 10,406,326 B2 | 9/2019 | Solomon | |
| 10,441,752 B2 | 10/2019 | Bierman et al. | |
| 10,569,059 B2 | 2/2020 | Bierman | |
| 10,682,157 B2 | 6/2020 | Bierman et al. | |
| 10,828,465 B2 | 11/2020 | Keyser et al. | |
| 10,850,069 B2 | 12/2020 | Solomon | |
| 11,318,286 B2 | 5/2022 | Sutton et al. | |
| 11,324,939 B2 | 5/2022 | Solomon et al. | |
| 2004/0092879 A1 | 5/2004 | Kraus et al. | |
| 2004/0097880 A1 | 5/2004 | Schur | |
| 2004/0193109 A1 | 9/2004 | Prestidge et al. | |
| 2004/0193118 A1 | 9/2004 | Bergeron | |
| 2004/0236287 A1 | 11/2004 | Swenson et al. | |
| 2005/0131350 A1 | 6/2005 | Shaw et al. | |
| 2005/0187524 A1 | 8/2005 | Willis et al. | |
| 2005/0256460 A1 | 11/2005 | Rome et al. | |
| 2006/0200083 A1 | 9/2006 | Freyman et al. | |
| 2007/0161940 A1 * | 7/2007 | Blanchard | A61M 25/0075 604/6.1 |
| 2007/0225647 A1 | 9/2007 | Luther et al. | |
| 2007/0250037 A1 | 10/2007 | Brimhall et al. | |
| 2007/0270751 A1 | 11/2007 | Stangenes et al. | |
| 2007/0282268 A1 | 12/2007 | Mayse | |
| 2008/0015539 A1 | 1/2008 | Pieroni et al. | |
| 2008/0027389 A1 | 1/2008 | Hiejima | |
| 2008/0039802 A1 | 2/2008 | Vangsness et al. | |
| 2008/0092571 A1 | 4/2008 | Allison et al. | |
| 2008/0093571 A1 | 4/2008 | Desecki | |
| 2008/0108944 A1 | 5/2008 | Woehr et al. | |
| 2008/0172003 A1 | 7/2008 | Plishka et al. | |
| 2009/0209912 A1 | 8/2009 | Keyser et al. | |
| 2009/0209914 A1 | 8/2009 | Koch et al. | |
| 2009/0234290 A1 | 9/2009 | Fisher et al. | |
| 2009/0287154 A1 | 11/2009 | Harding et al. | |
| 2010/0331787 A1 * | 12/2010 | Fournie | A61M 39/1011 604/207 |
| 2011/0056569 A1 | 3/2011 | Chambo et al. | |
| 2011/0257590 A1 | 10/2011 | Winsor et al. | |
| 2012/0041371 A1 | 2/2012 | Tal et al. | |
| 2012/0150118 A1 | 6/2012 | Keyser et al. | |
| 2012/0221024 A1 | 8/2012 | Sutton et al. | |
| 2013/0204226 A1 | 8/2013 | Keyser | |
| 2014/0058357 A1 | 2/2014 | Keyser et al. | |
| 2014/0275795 A1 | 9/2014 | Little et al. | |
| 2014/0276432 A1 | 9/2014 | Bierman et al. | |
| 2015/0038910 A1 | 2/2015 | Harding et al. | |
| 2015/0148756 A1 | 5/2015 | Lynn | |
| 2015/0265827 A1 | 9/2015 | Keyser et al. | |

(56) References Cited

U.S. PATENT DOCUMENTS

| | | |
|---|---|---|
| 2015/0306368 A1 | 10/2015 | Lin et al. |
| 2016/0228654 A1 | 8/2016 | Rozwadowski et al. |
| 2016/0271370 A1 | 9/2016 | Keyser et al. |
| 2017/0326341 A1 | 11/2017 | Liska |
| 2018/0064912 A1 | 3/2018 | Keyser et al. |
| 2018/0126125 A1 | 5/2018 | Hall et al. |
| 2019/0038889 A1 | 2/2019 | Keyser et al. |
| 2019/0060616 A1 | 2/2019 | Solomon |
| 2019/0351210 A1 | 11/2019 | Solomon et al. |
| 2020/0016375 A1 | 1/2020 | Solomon |
| 2020/0061346 A1 | 2/2020 | Solomon |
| 2020/0324088 A1* | 10/2020 | Harding ............ A61M 25/0097 |
| 2021/0031009 A1 | 2/2021 | Solomon |
| 2021/0268238 A1 | 9/2021 | Solomon et al. |
| 2021/0290911 A1 | 9/2021 | Hentzler et al. |
| 2022/0001146 A1 | 1/2022 | Hentzler et al. |
| 2022/0280767 A1* | 9/2022 | Solomon ............ A61M 25/0606 |
| 2022/0296859 A1* | 9/2022 | Sutton ............... A61M 25/0693 |

FOREIGN PATENT DOCUMENTS

| | | | |
|---|---|---|---|
| EP | 0653220 | 5/1995 | |
| EP | 1291035 | 3/2003 | |
| FR | 2655859 | 6/1991 | |
| FR | 2687320 | 8/1993 | |
| JP | 07-136285 | 5/1995 | |
| JP | 09-047512 | 2/1997 | |
| JP | 2007-260218 | 10/2007 | |
| JP | 2011-234802 | 11/2011 | |
| TW | 368422 | 9/1999 | |
| TW | 592741 | 6/2004 | |
| WO | WO 1992/016248 | 10/1992 | |
| WO | WO-9302734 A1 * | 2/1993 | ........ A61M 39/0606 |
| WO | WO-9830276 A1 * | 7/1998 | ........ A61M 39/0606 |
| WO | WO 2003/013627 | 2/2003 | |
| WO | WO 2009/091514 | 7/2009 | |
| WO | WO 2013/119557 | 8/2013 | |
| WO | WO-2019046456 A1 * | 3/2019 | ........ A61M 25/0606 |
| WO | WO 2022/178506 | 8/2022 | |

* cited by examiner

METHODS AND DEVICES FOR VASCULAR ACCESS

CROSS-REFERENCE TO RELATED APPLICATIONS

This application claims priority to U.S. Patent Application No. 63/367,403 filed Jun. 30, 2022, the content of which is incorporated herein by reference in its entirety.

FIELD OF THE INVENTION

The present disclosure is directed to valve assemblies having improved ability to selectively allow flow of fluids through the medical device and prevent leakage of fluids from the proximal end of the device. Such improved valve assemblies also prevent leakage of fluids after repeated insertion and removal of medical instruments through the valve, such as catheters, introducers, tubes, lines, and ports that can be used for vascular or other devices. The valve assemblies can also be used as a connection for needles (e.g., fistula needles), hemodialysis circuits, feeding tubes, urinary drain catheters, or any other suitable means.

BACKGROUND

Catheters allow medical practitioners to administer infusion or removal of fluids from a patient. For example, catheters can function as a conduit that allows infusion of fluids, such as normal saline solution, therapeutic substances, and/or nutritional fluids into a patient. Alternatively, catheters can withdraw fluids such as blood or other bodily fluids as required by the particular medical procedure. In those cases where the medical practitioner intends to position the catheter into a vessel, the medical practitioner will look for a flow of blood back into the catheter ("flashback") to verify placement of the catheter opening into a vessel. The number of different catheter insertion procedures and techniques is great and may include the use of a needle, dilator, stylet, or other medical devices within the catheter when placed.

Once properly positioned, the catheter's hub (or medical device positioned within the catheter) can be coupled to an adapter (typically a luer fitting) to enable fluid coupling of the catheter to the source of fluids or reservoir. However, in the case of an accidental disconnection between the catheter and the reservoir, there is a possibility for the patient to bleed out or to entrain air that will lead to an embolism, both of which are potentially life-threatening for the patient. Accidental disconnection can occur if the mating parts are not securely tightened. The mating parts can also become loose from patient movement, unwanted fidgeting, or other patient interference. Further, if the patients have any blood-borne pathogen (e.g., HIV, hepatitis, etc.), blood exposure for the caregiver is potentially lethal. As such, insertion of the catheter requires that the point of access remains sanitary. The period between insertion of the catheter and coupling of an adaptor can cause bodily fluids to escape through the catheter, causing an unsanitary condition for the medical practitioner who must handle the catheter for coupling of the adapter and/or remove the medical device inserted through the catheter. The caregiver often covers an open connection port with their finger to reduce the blood flow until making a mating connection. Since blood can be a medium for bacterial growth, infection chances can rise due to exposure at the time of catheter insertion.

As such, there remains a need for a valve assembly that permits controlled fluid flow that also reduces risk of infection by providing a tight seal with respect to the catheter. There also remains a need for a valve that slows blood loss to give the caretaker time to adequately clean the connection and wipe away any residual blood on the connection. There also remains a need for a valve that minimizes the blood exposure for the caregiver at the time of insertion, removal, or a change in catheters.

SUMMARY

The illustrations and variations described herein are meant to provide examples of the methods and devices of the invention. It is contemplated that combinations of aspects of specific embodiments or combinations of the specific embodiments themselves are within the scope of this disclosure. The valve assemblies described herein can be used in any tubing assembly, especially medical tubing not only limited to catheter assemblies.

A catheter assembly configured for use with a male luer is provided. The catheter assembly can comprise a catheter hub having an interior chamber and a valve located in the interior chamber. The valve can comprise a distal portion, a proximal portion, and a sidewall extending therebetween to define a valve interior. The valve can include a barrier layer having an arcuate shape that extends in the valve interior from the sidewall at the distal portion. The barrier layer can have at least one slit extending therethrough that is in a normally closed configuration to prevent a fluid from passing through the barrier layer.

The catheter assembly can further comprise a sealing ring located circumferentially at a distal end of the valve distally to the barrier layer. The sealing ring can have an exterior sealing surface that forms a seal between the valve and the interior chamber at the distal end. An exterior diameter of the valve can be smallest at a recessed portion located between the sidewall and the barrier layer and proximally adjacent to the exterior sealing surface. The recessed portion can be configured to provide deformation of the valve. A thickness of the sidewall at the recessed portion can be less than a thickness of the barrier layer.

The catheter assembly can further comprise a protrusion on an exterior surface of the sidewall. The protrusion can be located proximally to the recessed portion. The protrusion can nest within an opening in the interior chamber such that upon insertion of the luer into the proximal portion of the valve, the protrusion reinforces an adjacent sidewall to reduce elastic deformation of the valve at the protrusion and causing increased outward elastic deformation of the sidewall at the recessed portion. Further distal advancement of the luer can cause elastic deformation of the barrier layer opening the at least one slit such that the fluid can pass through the barrier layer.

The sealing ring can comprise a rounded edge along a sealing ring circumference. A plurality of protrusions can be provided on the exterior surface of the sidewall. The plurality of protrusions can each couple with a plurality of openings within the interior chamber. A lubricant within the interior chamber can be further provided. The sealing ring can remain engaged with an inner surface of the chamber when the male luer engages the recessed portion. The valve can comprise a flange at a proximal end. The flange can engage with a proximal end of the catheter hub. A thickness of the sidewall can be less than the thickness of the barrier layer.

The present disclosure is related to the following commonly assigned patents and applications, the entirety of each of which is incorporated by reference: U.S. Pat. No. 11,324, 939 issued on May 10, 2022; U.S. Pat. No. 8,105,288 issued on Jan. 31, 2012; U.S. Pat. No. 8,591,469 issued on Nov. 26, 2013; U.S. Pat. No. 9,775,973 issued on Oct. 3, 2017; U.S. Pat. No. 9,604,035 issued on Mar. 28, 2017; U.S. Pat. No. 10,828,465 issued on Nov. 10, 2020; U.S. publication nos.: US20200016375A1 published on Jan. 16, 2020, and US20210031009A1 published on Feb. 4, 2021; Provisional application Nos.: 62/993,493 filed on Mar. 23, 2020; 63/037, 496 filed on Jun. 10, 2020; and 63/037,841 filed on Jun. 11, 2020.

BRIEF DESCRIPTION OF THE DRAWINGS

Each of the following figures diagrammatically illustrates aspects and variations to better understand the invention. Variation of the invention from the aspects shown in the figures is contemplated.

DETAILED DESCRIPTION

For a better understanding of the present invention, reference will be made to the following description of the embodiments, which is to be read in association with the accompanying drawings, which are incorporated in and constitute a part of this specification, show certain aspects of the subject matter disclosed herein and, together with the description, help explain some of the principles associated with the disclosed implementations.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising. (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Figure 1A:
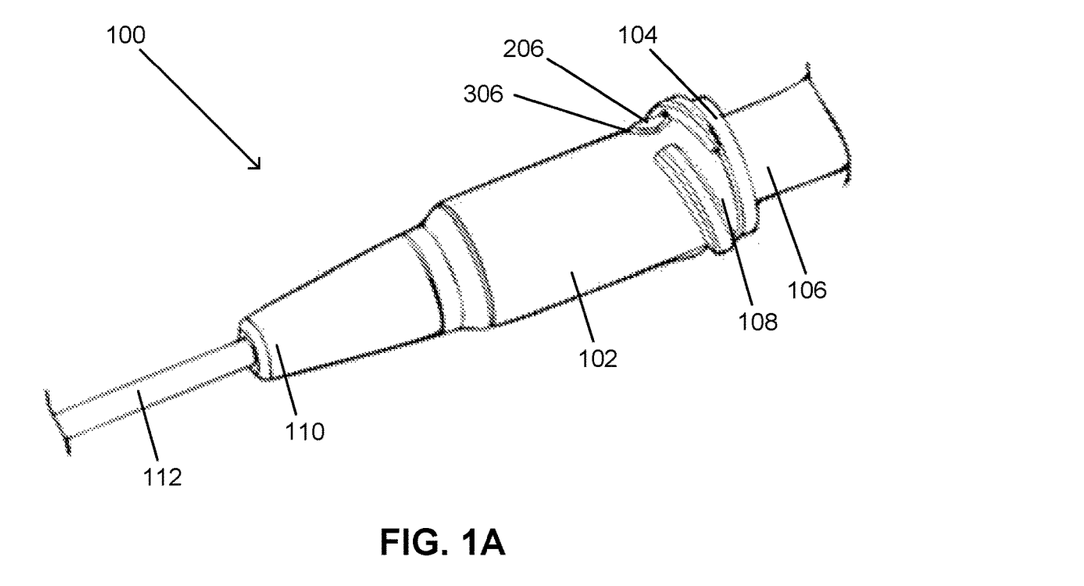
FIG. 1A shows a perspective view of a variation of an improved catheter-valve assembly.
Figure 1B:
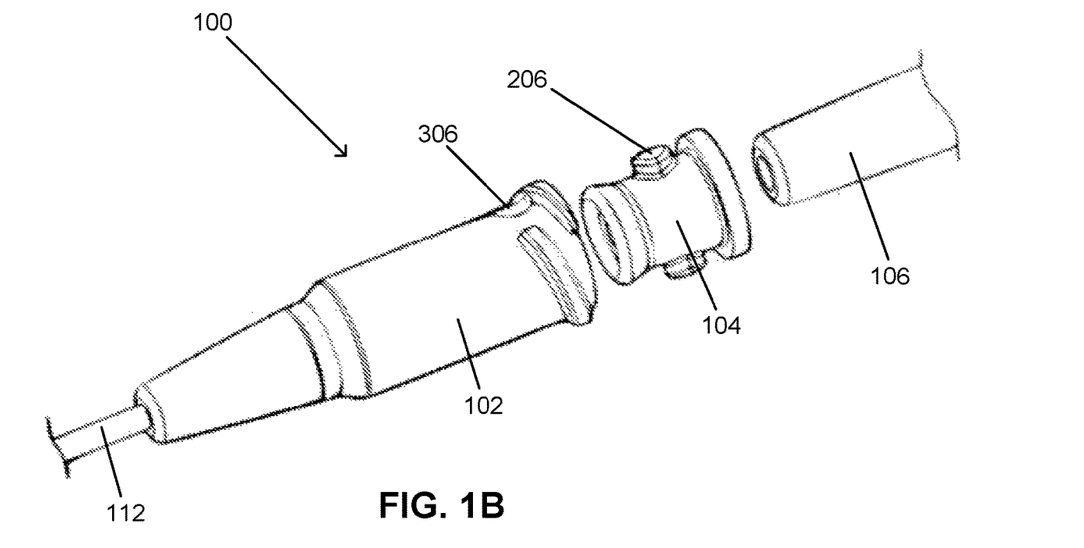
FIG. 1B shows an exploded view of the assembly of FIG. 1A
Figure 2A:
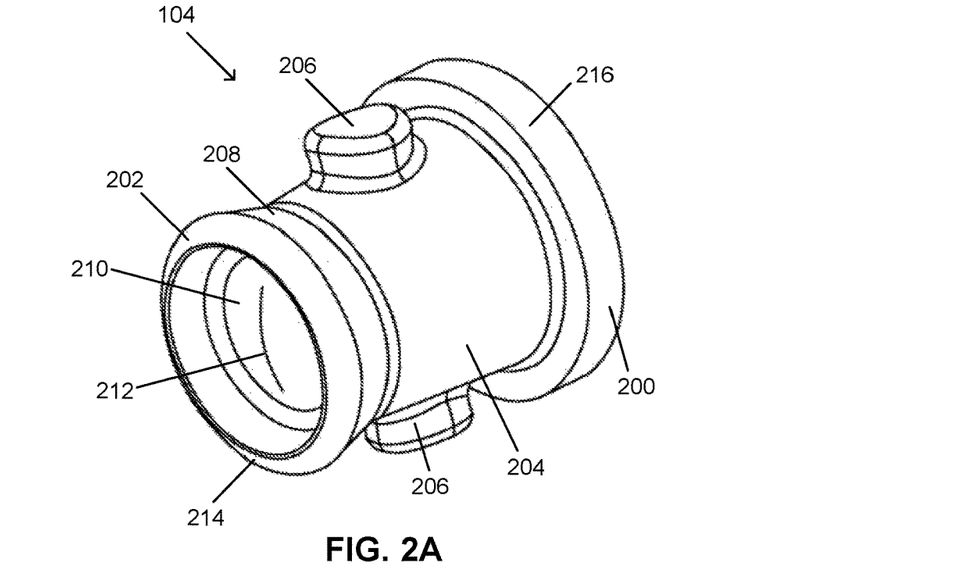
FIG. 2A shows a perspective view of one variation of a valve.
Figure 2B:
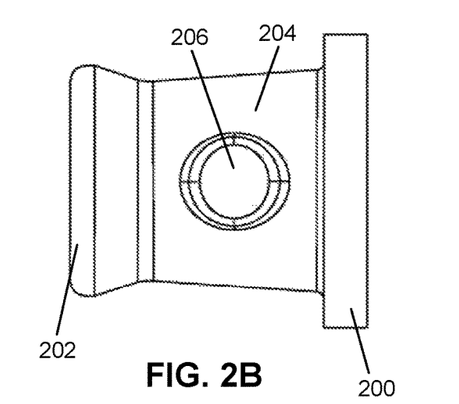
FIG. 2B shows a top view of the valve of FIG. 2A.
Figure 2C:
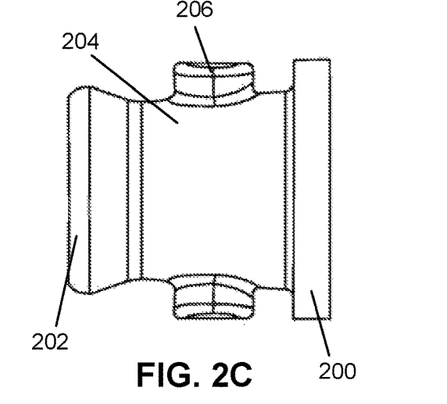
FIG. 2C shows a side view of the valve of FIG. 2A.
Figure 2D:
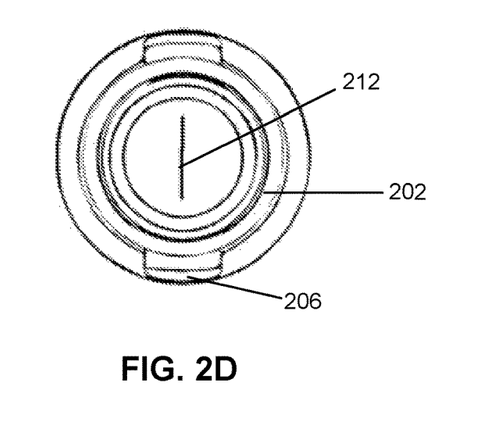
FIG. 2D shows a front view of the valve of FIG. 2A.
Figure 2E:
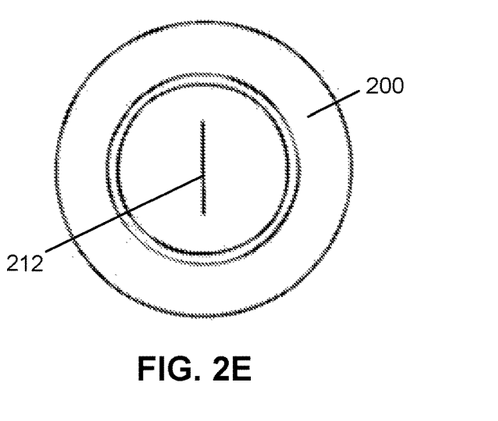
FIG. 2E shows a rear view of the valve of FIG. 2A.

FIG. 1A shows catheter-valve assembly 100 having a catheter hub 102, a valve 104, and a male luer 106 inserted therethrough. The catheter hub 102 can comprise a proximal end 108 and a distal end 110. A catheter tubing 112 can be coupled to the catheter and can extend from the distal end 110. As seen in FIG. 1B and further described herein, the valve 104 is seated in the open proximal end 108 of the catheter hub 102 so that the male luer 106 can then be inserted through a proximal end of the valve 104. The male luer 106 can be part of a medical device, such as a needle or other fluid source. As discussed below, the catheter hub 102 can include a pocket or hole 306 that nests protrusion 206 on the valve 104. The pocket 306 can extend partially within the catheter hub 102 or can extend through the catheter hub 102 forming a hole 306 as shown in FIGS. 1A and 1B.

FIGS. 2A to 2E show a valve having proximal end 200, distal end 202, and a sidewall 204 therebetween. In this variation, the sidewall can have protrusions 206 positioned on the outer surface of the valve 104. Protrusions 206 can be on either side of the sidewall 204 and can be circular, though other shapes can be considered. Additionally, the valve 104 can have a recessed portion 208 distal to the protrusions 206 and the sidewall 204. The recessed portion 208 is located where the valve 104 has its smallest exterior diameter and allows the valve 104 to deform when engaged by the male luer 106. While the figure shows two protrusions 104, any number of protrusions are within the scope of this disclosure.

The valve 104 includes a barrier layer 210 that extends from the sidewalls in an interior of the valve to prevent fluid flow. Variations of the valve 104 comprise barrier layers 210 that are opened through elastic deformation rather than pressure within the catheter assembly. For example, variations of the valves 104 require the male luer 106 to elastically deform the valve 104 and/or barrier layer 210 to permit fluid flow through the valve 104. In one additional variation, the barrier layer includes an arcuate or concave shape in an interior of the valve. The barrier layer 210 includes at least one slit 212 extending therethrough and has a normally closed configuration to prevent a fluid from passing therethrough the barrier layer 210. Alternatively, the barrier layer 210 can have a plurality of slits 212 that form a plurality of leaflet structures or flaps that open upon deformation of the valve 104.

The barrier layer 210 generally includes a flexible or semi-flexible material that is compatible with exposure to blood, medicaments, and other fluids commonly encountered during catheterization/infusion procedures. The valve 104 can be fabricated from a compliable and resilient material such that insertion of the male luer 106 causes the barrier layer 210 to stretch and deform to an open configuration.

In an additional variation, a distal end 202 of a valve 104 can have a sealing ring 214 located circumferentially around the valve and distally to the barrier layer 210. The sealing ring 214 can have an exterior sealing surface that forms a seal between the valve 104 and the hub 102 at the distal end 202 of the valve. The sealing ring 214 will be circumferentially engaged with the inner surface of the hub 102 such that the sealing ring 214 maintains a seal during insertion of the male luer 106, ensuring that fluid does not pass from the catheter hub 102 to an outer surface of valve 104. Variations of the valve can include a sealing ring 214 that is made of the same material as the remainder of the valve 104. Alternatively, the sealing ring 214 can comprise a different material than the remainder of the valve. Additionally, the angle at which the sealing ring 214 is offset with respect to the longitudinal axis can be changed to compress the valve 104 with respect to the hub 102 at varying diameters.

Figure 3A:
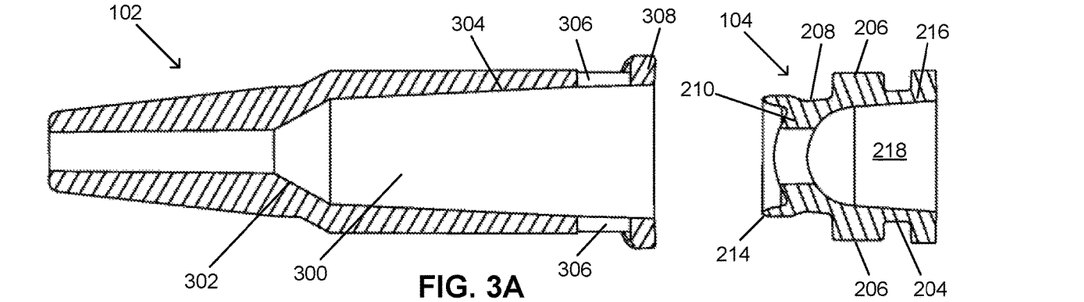
FIGS. 3A and 3B show cross-sectional side views of a catheter hub and the valve of FIG. 1A.
Figure 3B:
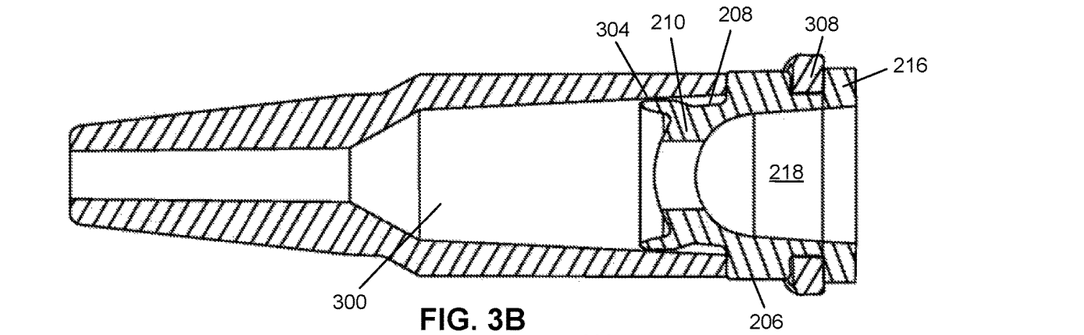
Figure 3C:
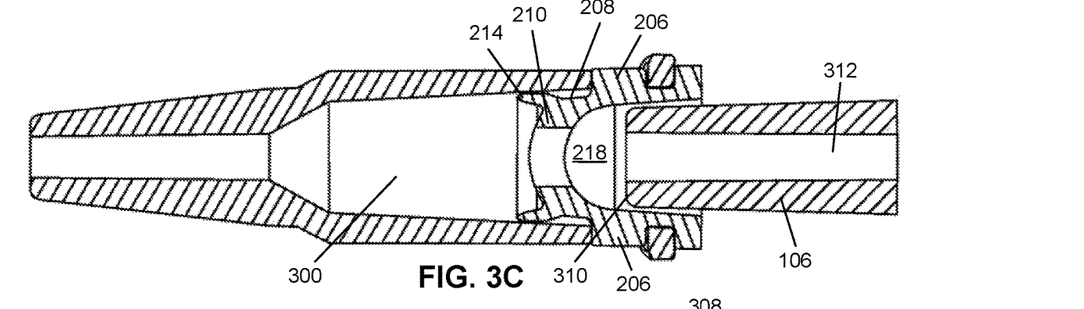
FIGS. 3C and 3D show cross-sectional side views of a catheter hub and the valve of FIG. 1A with a male luer introduced therein.

As seen in FIG. 3A, the catheter hub 102 has a chamber 300 extending from a proximal surface at the proximal end 108. The chamber 300 is in fluid communication with a catheter tubing 112 (FIGS. 1A and 1B) that is coupled to the hub 102. Variations of the chamber 300 can have straight walls or the walls can be tapered at an angle and can also have a tapered section 302 forming a female luer shape. The valve 104 exterior engages an inner surface 304 of the chamber 300 when the valve is inserted in the chamber, as seen in FIG. 3B. As shown in FIGS. 3B and 3C, the recessed portion 208 is offset from the inner surface 304 of the chamber 300. This offset in combination with the reinforcement of the valve wall adjacent to the protrusion 206 causes most of the deformation of the valve to occur at the recessed portion 208 of the wall distally to the protrusion.

Variations of the catheter hub 102 can comprise pockets or openings 306 positioned near the proximal end 108 of the hub 102, which seat the protrusions 206 of the valve 104 when the valve 104 is located in the chamber 300. Positioning of the valve 104 in the chamber 300 can occur via insertion or via molding of the valve into the chamber 300. As noted above, the protrusions 206 reinforce the sidewall 204 at the protrusions 206 to increase outward elastic deformation of the sidewall 204 at the recessed portion 208. The protrusions 206 nest in the openings 306 to hold the valve 104 in place such that the valve 104 to limit longitudinal stretching of the valve wall adjacent to the protrusion. This effect creates a preferential zone for stretching and/or deformation of the valve to open the barrier layer.

Protrusions 206 can additionally have a protrusion sealing ring that can provide additional interference along the openings 306. An outer portion of the protrusion where the protrusion 206 meets the edge of opening 306 accommodates the protrusion sealing ring. The protrusion sealing ring has a greater diameter than the remainder of the protrusion in order to provide a seal against the openings 306 of the hub 102. This seal, similar to sealing ring 214, prevents leaking of any fluid through the assembly.

Both the hub 102 and the valve 104 can comprise flanges, 216, 308 respectively, at their respective proximal ends that engage each other when the protrusions 206 nest within the openings 306. The valve flange portion 216 comprises a diameter greater than a diameter of the sidewall 204 for sealing against a proximal surface of the catheter hub flange 308. Alternatively, in some variations the valve flange portion 216 can include openings or segments such that it is not circumferentially continuous about the sidewall 204.

Figure 3D:
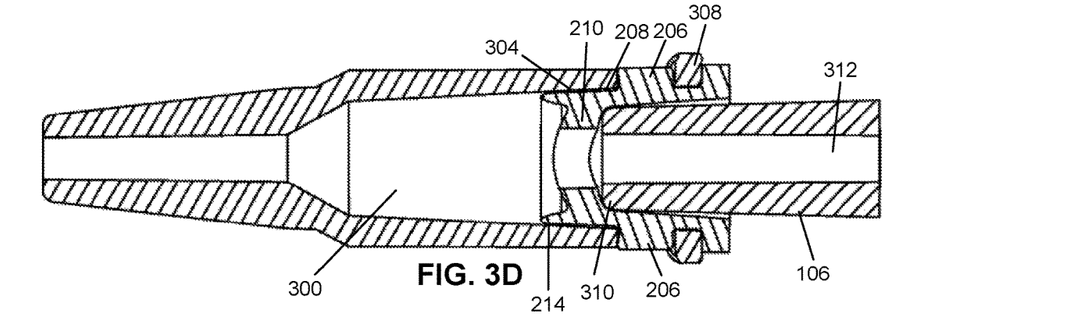

As seen in FIG. 3C, the male luer 106 is inserted into a valve interior 218 of the valve 104 and ultimately engages the walls/septum to elastically stretch the valve to open the barrier layer 210. The variations of the valve shown in FIG. 3C includes a valve interior 218 that is concave near the recessed portion 208 and includes walls with a tapered angle on the exterior and/or interior. During insertion, a distal end 310 of the male luer 106 can engage with the recessed portion 208 of the valve 104, as seen in FIG. 3D, causing the barrier layer 210 to open in a distal direction. Upon engagement and advancement of the luer, the barrier layer can undergo elastic deformation, opening the at least one slit 212 such that the fluid can pass through the barrier layer 210 and into a lumen 312 of the male luer 106. The valve interior 218 and male luer 106 can be provided with a small clearance therebetween to allow for easier longitudinal movement of the luer 106 within when the valve 104 diameter at the protrusions 206 decreases during insertion of the luer 106. In some variations, insertion of the male luer 106 into the valve interior 218 can cause the distal end of the barrier layer 210 to a fully open position, while the lateral surface of the male luer 106 engages the sidewall 204 of the valve 104. However, in alternate variations, the barrier layer 210 can merely deflect to allow sufficient fluid flow.

In additional variations of a valve, the thickness of the barrier layer 210 is greater than a thickness of the sidewall 204 at the recessed portion 208 as well as a thickness of the sidewall (excluding the regions where the protrusion 206 joins the sidewall). For example, the increased thickness of the barrier layer 210 permits the slit 212 to elastically return to a closed position once luer 106 is removed. The relatively thinner sidewall 204 reduces an offset distance between the internal diameter of the valve interior 218 and the inner surface 304 of chamber 300. Reducing this offset distance allows for insertion of the male luer 106 to a sufficient depth along a longitudinal axis to open the slit 212 at the barrier layer 210 of the valve 104 without being impeded by the sidewall 204 of the valve 104. For example, if the sidewall 204 is too thin, then the valve 104 can suffer from an increased risk of failure (e.g., cracking or splitting). The thickness of the barrier layer 210 increases relative rigidity in comparison with the remainder of the valve 104, allowing the slit 212 to close fully, increasing the likelihood that the slit returns to its original state to close the valve 104, preventing leakage. In some variations, the thickness differential also allows deformation of the valve to occur at the barrier layer rather than the sidewall or recessed portion 208.

Figure 4A:
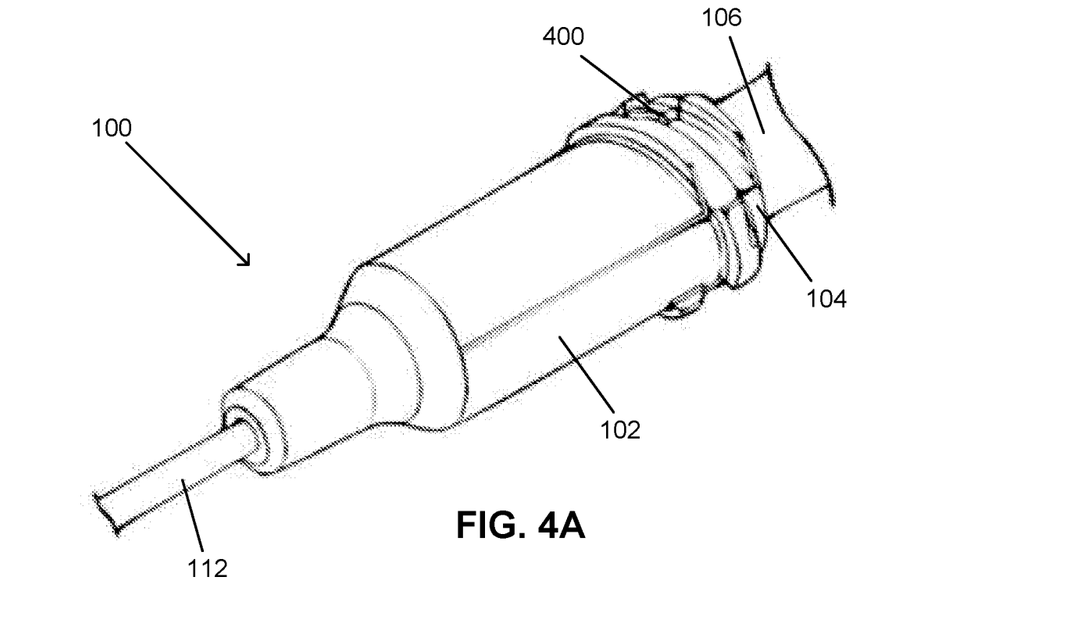
FIG. 4A shows a perspective view of another variation of an improved catheter-valve assembly.
Figure 4B:
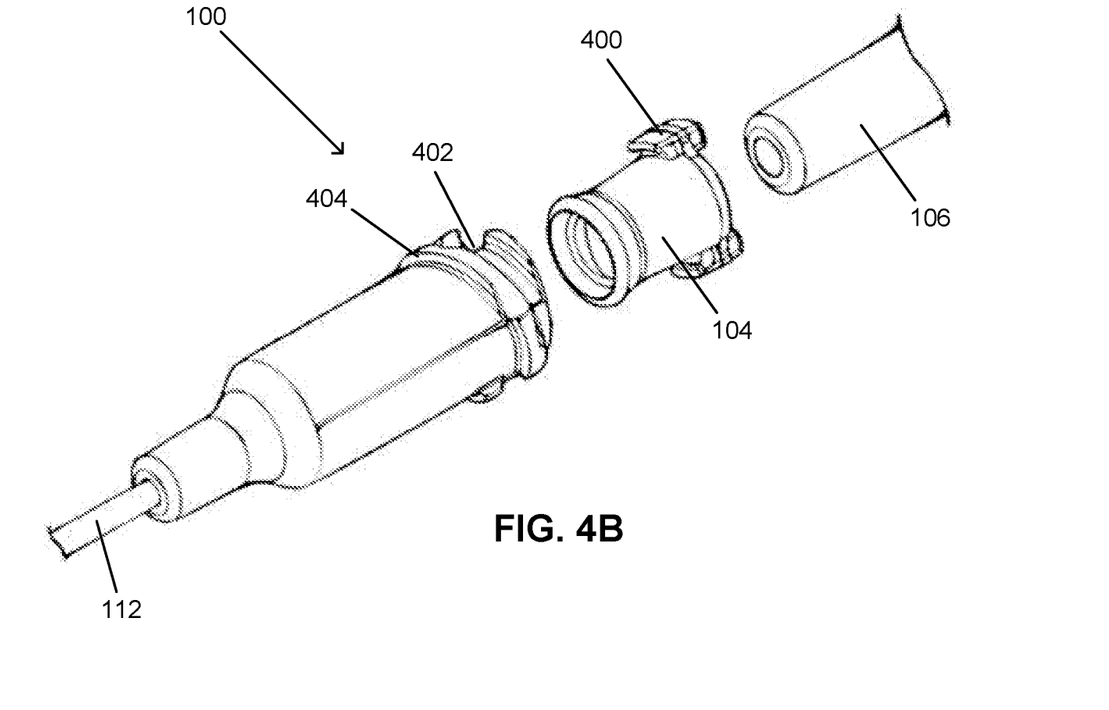
FIG. 4B shows an exploded view of the assembly of FIG. 4A
Figure 4C:
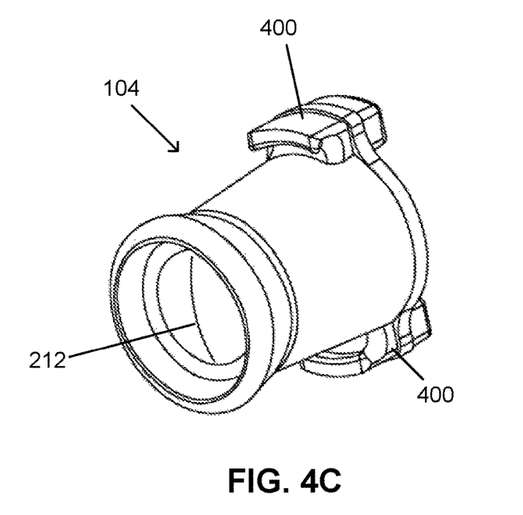
FIG. 4C shows a perspective view of the valve of FIG. 4A.
Figure 4D:
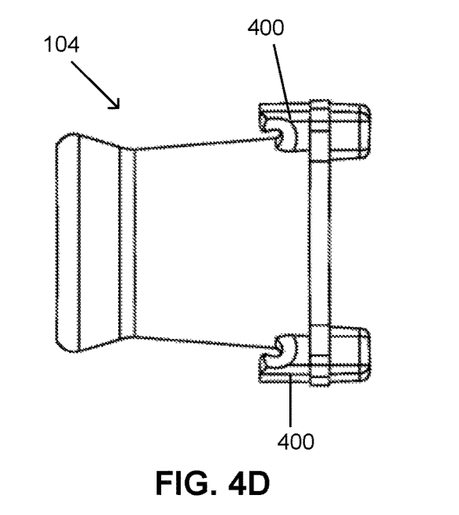
FIG. 4D shows a side view of the valve of FIG. 4A.
Figure 4E:
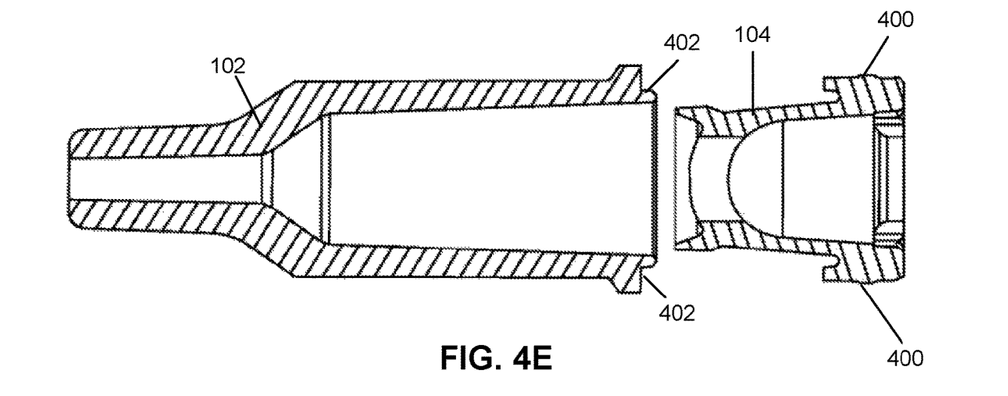
FIG. 4E shows a cross-sectional side view of another variation of the catheter hub and the valve of FIG. 4A.
Figure 4F:
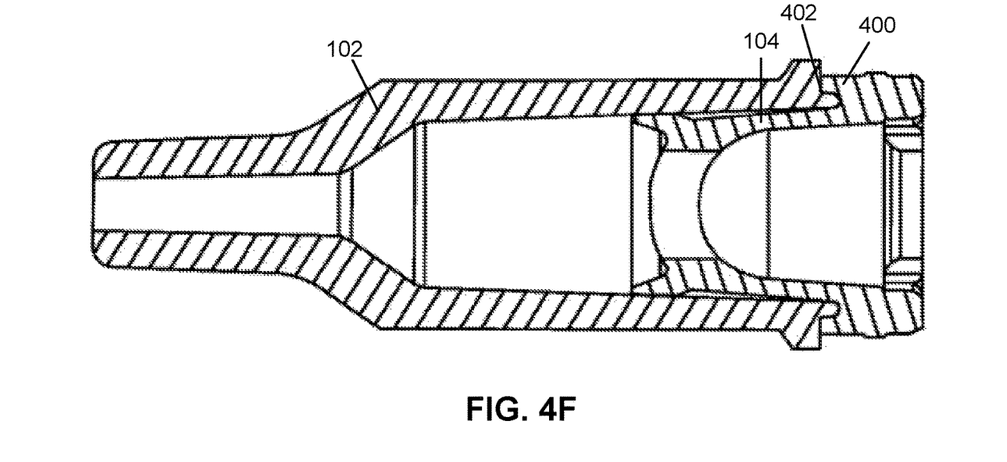
FIG. 4F shows a cross-sectional side view of another variation of the catheter hub and the valve of FIG. 4A with a male luer introduced therein.
Figure 4G:
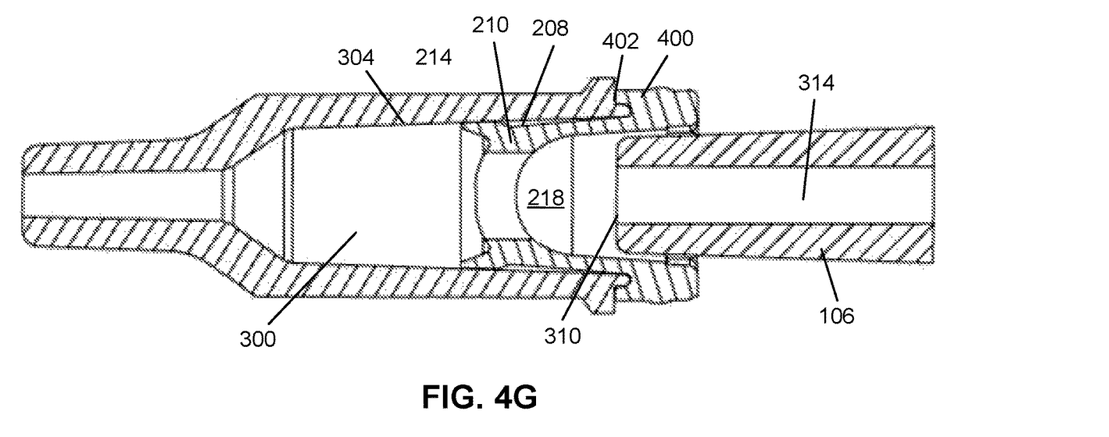
FIGS. 4G and 4H show cross-sectional side views of a catheter hub and the valve of FIG. 4A with a male luer introduced therein.
Figure 4H:
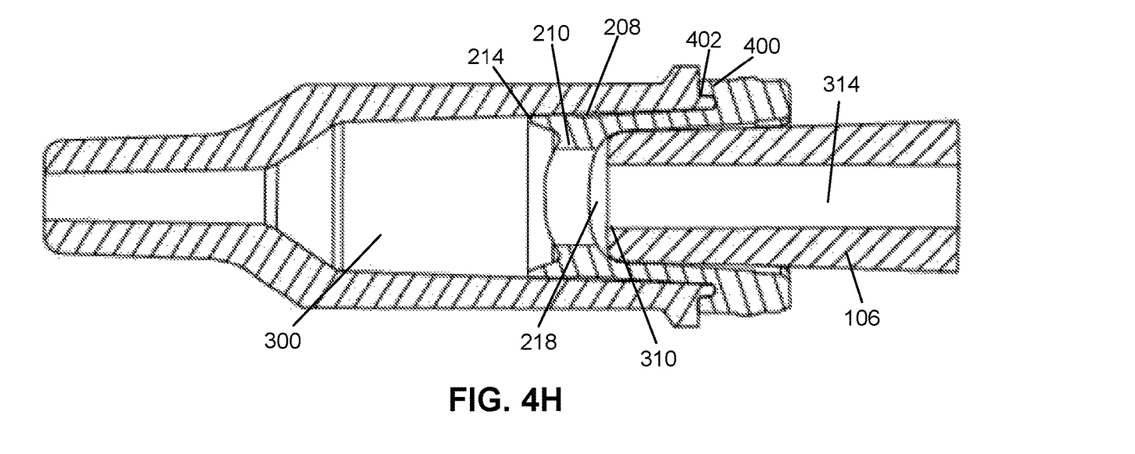

FIGS. 4A to 4H show various views of another variation of a catheter-valve assembly. In this variation, the valve 104 can have one or more lips 400 on a proximal end 200. The lips 400 can engage with one or more recesses 402 on the catheter hub 102, as seen in FIGS. 4G and 4H. Upon engagement with the recesses 402, the lips 400 can overhang onto the recesses 402 on the hub 102 to secure the valve 104 onto the hub 102 for use with the male luer 106 or another medical device. In another variation of the device, threads 404 on the catheter hub 102 can be used to hold lips 400, preventing the valve 104 from being pushed in too far into the catheter hub 102.

Similar to the features in the variation shown in FIGS. 3A to 3D, the catheter hub 102 can have a chamber 300 extending from a proximal surface at the proximal end 108. The chamber 300 is in fluid communication with a catheter tubing 112 that is coupled to the hub 102. Variations of the chamber 300 can have straight walls or the walls can be tapered at an angle and can also have a tapered section 302 forming a female luer shape. The valve 104 exterior engages an inner surface 304 of the chamber 300 when the valve is inserted in the chamber, as seen in FIG. 4G. As shown in FIG. 4G, the recessed portion 208 is offset from the inner surface 304 of the chamber 300. This offset causes most of the deformation of the valve to occur at the recessed portion 208 of the wall.

As seen in FIGS. 4G and 4H, the male luer 106 is inserted into a valve interior 218 of the valve 104 and ultimately engages the walls/septum to elastically stretch the valve to open the barrier layer 210. The variations of the valve shown in FIGS. 4G and 4H includes a valve interior 218 that is concave near the recessed portion 208 and includes walls with a tapered angle on the exterior and/or interior. During insertion, a distal end 310 of the male luer 106 engages with the recessed portion 208 of the valve 104, as seen in FIG. 4H, causing the barrier layer 210 to open in a distal direction. Upon engagement and advancement of the luer, the barrier layer can undergo elastic deformation, opening the at least one slit 212 such that the fluid can pass through the barrier layer 210 and into a lumen 312 of the male luer 106. The valve interior 218 and male luer 106 can be provided with a small clearance therebetween to allow for easier longitudinal movement of the luer 106 within when the valve 104 diameter decreases during insertion of the luer 106. In some variations, insertion of the male luer 106 into the valve interior 218 can cause the distal end of the barrier layer 210 to a fully open position, while the lateral surface of the male luer 106 engages the sidewall 204 of the valve 104. However, in alternate variations, the barrier layer 210 can merely deflect to allow sufficient fluid flow.

In additional variations of a valve, the thickness of the barrier layer 210 is greater than a thickness of the sidewall 204 at the recessed portion 208 as well as a thickness of the sidewall. For example, the increased thickness of the barrier layer 210 permits the slit 212 to elastically return to a closed position once luer 106 is removed. The relatively thinner sidewall 204 reduces an offset distance between the internal diameter of the valve interior 218 and the inner surface 304 of chamber 300. Reducing this offset distance allows for insertion of the male luer 106 to a sufficient depth along a longitudinal axis to open the slit 212 at the barrier layer 210 of the valve 104 without being impeded by the sidewall 204 of the valve 104. For example, if the sidewall 204 is too thin, then the valve 104 can suffer from an increased risk of failure (e.g., cracking or splitting). The thickness of the barrier layer 210 can increase relative rigidity in comparison with the remainder of the valve 104, allowing the slit 212 to close fully, increasing the likelihood that the slit returns to its original state to close the valve 104, preventing leakage. In some variations, the thickness differential also allows deformation of the valve to occur at the barrier layer rather than the sidewall or recessed portion 208.

The previous description of the disclosed embodiments is provided to enable any person skilled in the art to make or use the present invention. Various modifications to these embodiments will be readily apparent to those skilled in the art, and the generic principles defined herein can be applied to other embodiments without departing from the spirit or scope of the invention. For example, a wide variety of materials may be chosen for the various components of the embodiments. It is therefore desired that the present embodiments be considered in all respects as illustrative and not restrictive, reference being made to the appended claims as well as the foregoing descriptions to indicate the scope of the invention.

The invention claimed is:

1. A catheter assembly configured for use with a medical device, the catheter assembly comprising:
   a catheter hub having an interior chamber;
   a valve located in the interior chamber and comprising a distal portion, a proximal portion, and a sidewall extending therebetween to define a valve interior, the valve including a barrier layer that extends in the valve interior from the sidewall at the distal portion, the barrier layer having at least one slit extending therethrough that is in a normally closed configuration to prevent a fluid from passing through the barrier layer;
   a sealing ring located circumferentially at a distal end of the valve distally to the barrier layer, the sealing ring having an exterior sealing surface that forms a seal between the valve and the interior chamber at the distal end, wherein an exterior diameter of the valve is smallest at a recessed portion located between the sidewall and the barrier layer and proximally adjacent to the exterior sealing surface, the recessed portion being configured to provide deformation of the valve, and where a thickness of the sidewall at the recessed portion is less than a thickness of the barrier layer; and
   a plurality of protrusions spaced apart on the exterior surface of the sidewall and spaced from a front and a back of the sidewall, wherein the plurality of protrusions each nest with a plurality of openings within the interior chamber, such that upon insertion of the medical device into the valve, the plurality of protrusions reinforce an adjacent sidewall to reduce elastic deformation of the adjacent sidewall causing increased elastic deformation of an un-reinforced portion of the sidewall, wherein further distal advancement of the medical device causes elastic deformation of the barrier layer to open the at least one slit.

2. The catheter assembly of claim 1, wherein the sealing ring comprises a rounded edge along a sealing ring circumference.

3. The catheter assembly of claim 1, further comprising a lubricant within the interior chamber.

4. The catheter assembly of claim 1, wherein the sealing ring remains engaged with an inner surface of the chamber when the medical device engages the recessed portion.

5. The catheter assembly of claim 1, where a thickness of the sidewall is less than the thickness of the barrier layer.

6. The catheter assembly of claim 1, wherein the barrier layer has an arcuate shape.

7. The catheter assembly of claim 1, wherein the plurality of protrusions are aligned with a longitudinal direction of the at least one slit.

8. The catheter assembly of claim 1, further comprising a flange at the proximal portion of the valve, wherein the flange engages with a proximal end of the catheter hub.

9. A catheter assembly configured for use with a medical device, the catheter assembly comprising:
   a catheter hub having an interior chamber;
   a valve located in the interior chamber and comprising a distal portion, a proximal portion, and a sidewall extending therebetween to define a valve interior, the valve including a barrier layer that extends in the valve interior from the sidewall at the distal portion, the barrier layer having at least one slit extending therethrough that is in a normally closed configuration to prevent a fluid from passing through the barrier layer, wherein an exterior diameter of the valve is smallest at a recessed portion located between the sidewall and the barrier layer, the recessed portion being configured to provide deformation of the valve, and where a thickness of the sidewall at the recessed portion is less than a thickness of the barrier layer; and a plurality of protrusions spaced apart on the exterior surface of the sidewall and spaced from a front and a back of the sidewall, wherein the plurality of protrusions each nest with a plurality of openings within the interior chamber, such that upon insertion of the medical device into the valve, the plurality of protrusions reinforce an adjacent sidewall to reduce elastic deformation of the adjacent sidewall causing increased elastic deformation of an un-reinforced portion of the sidewall, wherein further distal advancement of the medical device causes elastic deformation of the barrier layer to open the at least one slit.

10. The catheter assembly of claim 9, further comprising a sealing ring located circumferentially at a distal end of the valve distally to the barrier layer, the sealing ring having an exterior sealing surface that forms a seal between the valve and the interior chamber at the distal end, wherein the sealing ring comprises a rounded edge along a sealing ring circumference.

11. The catheter assembly of claim 10, wherein the sealing ring remains engaged with an inner surface of the chamber when the medical device engages the recessed portion.

12. The catheter assembly of claim 9, further comprising a lubricant within the interior chamber.

13. The catheter assembly of claim 9, wherein the barrier layer has an arcuate shape.

14. The catheter assembly of claim 9, wherein the plurality of protrusions are aligned with a longitudinal direction of the at least one slit.

15. The catheter assembly of claim 9, further comprising a flange at the proximal portion of the valve, wherein the flange engages with a proximal end of the catheter hub.

\* \* \* \* \*